United States Patent [19]

Balde et al.

[11] 4,398,887
[45] Aug. 16, 1983

[54] DENTAL CROWN ASSEMBLY

[76] Inventors: John W. Balde, 35 Meadow La., Flemington, N.J. 08822; Irvin Vine, 32 Lafayette Rd., West Princeton, N.J. 08540

[21] Appl. No.: 310,803

[22] Filed: Oct. 13, 1981

Related U.S. Application Data

[63] Continuation of Ser. No. 126,040, Feb. 29, 1980, abandoned.

[51] Int. Cl.³ .............................................. A61C 5/08
[52] U.S. Cl. .................................... 433/218; 433/223
[58] Field of Search ................ 433/222, 218, 219, 223

[56] References Cited

U.S. PATENT DOCUMENTS

| | | | |
|---|---|---|---|
| 347,933 | 8/1886 | Grout | 433/219 |
| 472,344 | 4/1892 | Evans | 433/222 |
| 709,410 | 9/1902 | Kelly | 433/218 |
| 986,653 | 3/1911 | Supplee | 433/218 |
| 1,414,475 | 5/1922 | Kochmit | 433/183 |
| 2,537,142 | 1/1951 | Lankford et al. | 433/219 |
| 4,172,323 | 10/1979 | Orlowski | 433/180 |

Primary Examiner—John J. Wilson

[57] ABSTRACT

A two piece dental crown comprises cup-shaped inner (12) and outer (16) members, the inner member being adapted to be mounted on the occlusal portion of a tooth being capped, and the outer member being adapted to be mounted on the tooth including the inner member, the side wall (18) of the outer member extending beyond the side wall (20) of the inner member and into contact with the gingival portion of the tooth. In use, the inner and outer members are rigidly bonded together in slightly spaced apart relation. In one embodiment, a stiffening member is bonded to the two members in the space therebetween.

7 Claims, 3 Drawing Figures

DENTAL CROWN ASSEMBLY

This is a continuation of application Ser. No. 06/126,040 filed Feb. 29, 1980 now abandoned.

BACKGROUND OF THE INVENTION

This invention relates to dental crowns for teeth, and particularly to pre-formed crowns, generally of cup-shaped, which are intended to be custom fit to the tooth of a patient during a single dental visit.

Advantages of the use of such pre-formed crowns, in contrast with crowns which are cast from a mold of the tooth to be crowned, are that the crowns can be inexpensively mass produced, can be of a material, such as annealed stainless steel, which is far less expensive than the noble metals commonly found in custom cast crowns, and can be permanently fitted in a single, continuous procedure.

A disadvantage of such pre-formed crowns, however, is that because they are shaped on site, generally using simple hand tools, the material of the crowns must be relatively easily workable. This, in turn, requires that the walls of the crowns be ductile and relatively thin, which gives rise to problems of strength and durability, especially on the occlusal or biting surfaces. Thus, while the use of pre-formed crowns is less expensive and more convenient than the use of custom cast crowns, such pre-formed crowns generally require much earlier replacement due to premature wear or perforation.

SUMMARY OF THE INVENTION

A dental crown according to this invention comprises, in one embodiment, a two piece assembly including an inner, cup-shaped member adapted to be mounted and custom fit onto the occlusal portion of the tooth being capped, and an outer, cup-shaped member having a longer side wall than that of the inner member adapted to be mounted and custom fit onto the tooth and the inner member thereon, the side wall of the outer member extending beyond that of the inner member and into contact with the gingival portion of the tooth. When mounted on the tooth, both members are cemented to the tooth where they contact it, and both members are rigidly bonded together but in slightly spaced relation at the occlusal portions thereof.

In another embodiment, the spacing between the two members at their occlusal portions is maintained by a stiffening member bonded therebetween.

DETAILED DESCRIPTION

Figures 1, 3:
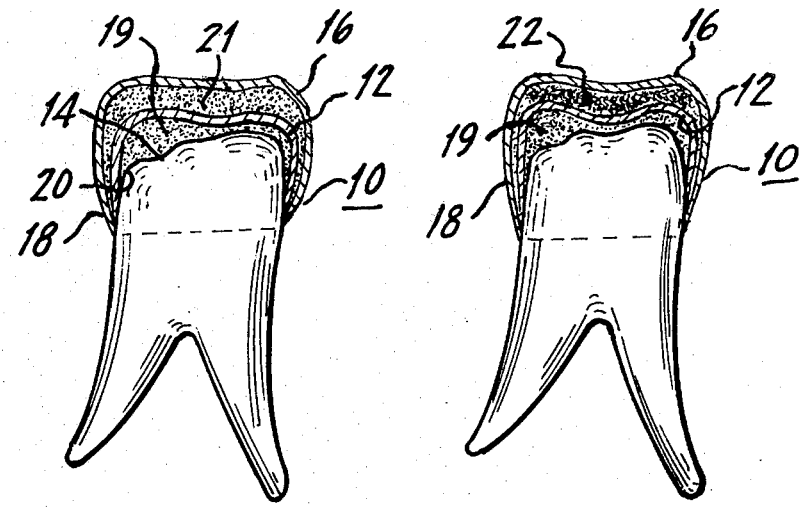
FIG. 1 is a view, in cross-section, of a crown assembly in accordance with this invention mounted on a tooth.
FIG. 3 is a view, in cross-section, of the crown assembly shown in FIG. 2 mounted on a tooth.

FIG. 1 shows a cross-sectional view of a dental crown according to the invention mounted on a tooth. The assembled crown 10 comprises a cup-shaped inner member 12 mounted on the occluding or biting surface of the tooth, and a cup-shaped outer member 16 rigidly bonded to the inner member 12. The outer member 16 is larger than the inner member and, as shown, the side wall 18 of the outer member 16 extends beyond the side wall 20 of the inner member into contact with the tooth at the gingival margin. The outer member 16 is formed, as in conventional practice, to conform to the shape of the tooth being crowned and to mate with the opposing tooth (not shown).

Disposed between the inner member 12 and the tooth surface is either a compliant filling cement 19 of the type generally used, e.g., a zinc oxide-ugenol type sedative cement, or a more permanent zinc phosphate or polycarboxylate cement. Disposed between the inner 12 and the outer 16 members, rigidly bonding them together in slightly spaced apart relation, is a strong and rigid bonding material 21, such as the aforementioned polycarboxylate cement or one of the cyanoacrylate resins.

As manufactured, i.e., prior to mounting thereof on a tooth, the relative dimensions of the two crown members 12 and 16 are such that the inner member fits or nests fairly snugly within the outer member, but not in a force fitting relationship. That is, the inner member is preferably readily slidable into and out of the outer member. While not critical, the clearance between the side walls of the two members, when in nested relationship, is preferably less than about 0.005 inch.

The thickness of the wall of each of the members 12 and 16 can be comparable to that of prior known pre-formed single piece crowns. Thus, the instant crowns are stronger and more durable than such prior crowns. In addition, however, owing to the bonding together of the two members, even greater strength is obtained at the critical occlusal surface than provided by the mere presence of the double walls of the crown. That is, the rigid bonding material 21 between the crown members serves much the same function as the cross or diagonal members of a truss beam, such cross members imparting, as generally known, significantly greater strength against bending and shearing forces than the longitudinal members themselves.

Up to a certain limit, the greater the spacing between the crown members, the greater is the strength of the crown. As a practical matter, however, the spacing between the members is limited by the space available to the crowned tooth in its relationship with the other teeth. Also, excessively thick layers of most bonding materials do not have good shear strength. Although not critical, spacings in the range of between 0.004 and 0.030 inch can be used.

Figure 2:
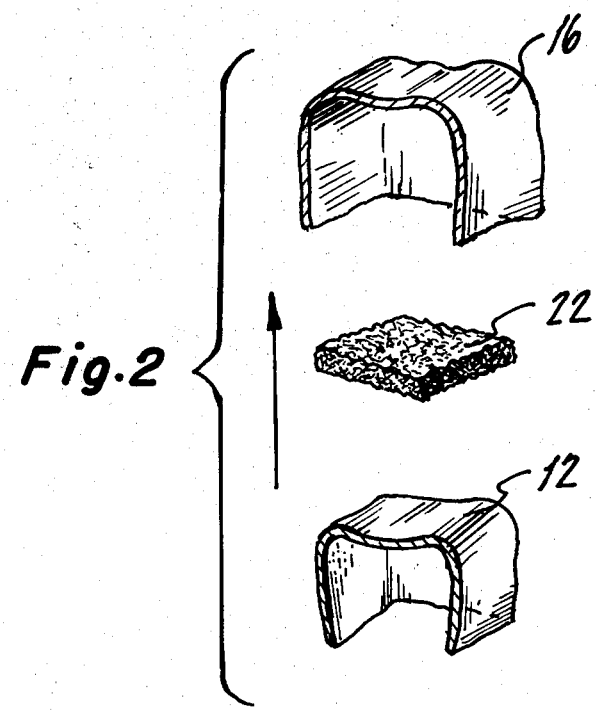
FIG. 2 is an exploded view of a different crown assembly in accordance with this invention, and using a stiffening member between the two crown members.

To even further strengthen the crown, a crown assembly as shown in FIGS. 2 and 3 can be used. This crown also comprises two cup-shaped members 12 and 16 such as those used in the FIG. 1 embodiment, and further includes a stiffening member 22 disposed between the two members at the occlusal surface portions 24 thereof. As shown in FIG. 2, the stiffening member 22 is of a generally sponge-like construction comprising, for example, a pad of fine meshed stainless steel filaments. Such pads are presently commercially available and are used, for example, as filters in industrial applications. The density of the pad is preferably such that the stiffening member has a number of passageways therethrough through which a bonding adhesive or cement can penetrate for impregnating the pad with the cement. Other porous materials can be used, such as known metal sheet-like structures of cellular or honeycomb construction.

In use, the adhesive impregnated stiffening member 22 is placed between the two crown members 12 and 16 for bonding them together into a rigid assembly. The stiffening member provides greater strength to the adhesive bond between the two members in the same manner that reinforcing rods or meshes provide greater strength to plaster or concrete aggregates.

In the mounting of the crown assembly on a tooth to be capped, the tooth is first prepared in usual fashion. Then, the inner member 12 is shaped to fit on the upper portion of the tooth. Usual techniques can be used, except that, as shown in FIG. 1, the inner member does not extend far along the walls of the tooth towards the gingival or root portion thereof.

Then, while the inner member is in place, the outer member is placed over the tooth and preliminarily shaped to provide a properly fitting crown. During this preliminary shaping, a precise mating relationship between the two members is established. Also, as shown in FIG. 1, the side wall 12 of the outer member extends beyond the side wall 20 of the inner member, and only the outer member side wall contacts the axial walls of the tooth. The reason for this is that great crown strength is not required at the walls of the tooth, and a double walled cap at the base portion would provide a poor fit with the side of the tooth and cause irritation to the gingiva.

Then, for the FIG. 1 embodiment crown, the two crown members are removed from the tooth and separated, a small quantity of adhesive 21 is placed inside the outer member, and the inner member is then nested into the outer member and properly mated therewith. A selected quantity of adhesive material 19 is then placed inside the crown, and the entire crown is remounted, as a unit, on the tooth.

Final positioning and seating of the crown is then immediately performed in accordance with customary procedures. Once the adhesive materials set-up, the rigidly bonded-together two piece crown assembly is extremely rigid and difficult to deform.

The spacing between the occlusal surface portions of the two members is determined primarily by the quantity of adhesive material used therebetween, only a small amount of the adhesive being squeezed downwardly between the side walls of the two members. The close fit of the side walls to each other limits the amount of adhesive passing therebetween. Some experience, therefore, on a trial and error basis is required by the dentist to determine the amount of adhesive to use in each instance. Notwithstanding this, the fitting of crown assemblies according to this invention, by shaping each member separately, is no more difficult than the shaping and fitting of prior known single piece crowns.

The fitting of the crown assembly shown in FIG. 2 is much the same, except that the strengthening or stiffening member 22 is preferably present during the initial fitting and shaping of the outer member on the tooth. As previously noted, the adhesive material can be applied to the stiffening member by immersing it in a fluid of the adhesive material, or the member can be pre-impregnated with an adhesive material which can be activated, in known manner, at the time of use. In either case, the quantity of adhesive material is closely controlled, and the spacing between the two crown members 12 and 16 is controlled by the thickness of the stiffening member 22.

The presence of the stiffening member, as previously noted, significantly increases the final strength of the crown assembly without adversely affecting the malleability during the fitting and installation process. The stiffener additionally serves to prevent cracking or crushing of the adhesive cement when the crown is subjected to severe forces.

What is claimed is:

1. A two-piece dental crown assembly adapted to be hand-tool shaped and conformed, in situ, to the shape of a tooth to be capped, characterized as comprising a shallow, generally cup-shaped inner member of a ductile material having one closed end adapted to be mounted on the occlusal portion of the tooth, and a deeper, generally cup-shaped outer member of a ductile material having one closed end disposed around said inner member, the side wall of the outer member being longer than that of the inner member and extending beyond the side wall of the inner member to contact and cover the side portions of the tooth when mounted on said tooth, and a bonding material between said members rigidly bonding together the closed ends thereof.

2. An assembly according to claim 1, characterized by including a stiffening member (22) dimensioned to fit between the closed ends of the two crown members, and adapted to be bonded thereto.

3. An assembly according to claim 2, characterized in that said stiffening member is of a mesh-like construction having a plurality of passageways therethrough.

4. An assembly according to claim 3 in which the stiffening member is pre-impregnated with an adhesive adapted to be activated when required.

5. A method of capping a tooth characterized by positioning a shallow, pre-formed generally cup-shaped inner member having a closed occlusal surface on the tooth to be capped and shaping the occlusal surface, disposing an outer cup-shaped member having one closed end and a greater depth than said inner member on the inner member capped tooth and shaping said outer member about said inner member and into close fitting contacting relation with the side wall of said tooth, removing and separating said members, disposing a bonding material in the base portion of said outer member, then inserting said inner member into said outer member to sandwich the bonding material therebetween, and mounting and bonding the assembled crown onto said tooth.

6. The method of claim 5 characterized by disposing between and bonding a stiffening member (22) to the occlusal portions of said inner and outer members.

7. The method of claim 6 characterized by using a stiffening member having a plurality of passageways therethrough, and impregnating said member with a bonding material prior to disposing it between said inner and outer members.

* * * * *